United States Patent [19]

Amkraut et al.

[11] Patent Number: 5,286,491
[45] Date of Patent: Feb. 15, 1994

[54] PREVENTION OF CONTACT ALLERGY BY COADMINISTRATION OF A CORTICOSTEROID WITH A SENSITIZING DRUG

[75] Inventors: Alfred Amkraut, Palo Alto; Jane E. Shaw, Atherton, both of Calif.

[73] Assignee: ALZA Corporation, Palo Alto, Calif.

[21] Appl. No.: 884,687

[22] Filed: May 18, 1992

Related U.S. Application Data

[60] Continuation of Ser. No. 753,284, Aug. 30, 1991, Pat. No. 5,171,576, which is a division of Ser. No. 604,840, Nov. 27, 1990, Pat. No. 5,077,054, which is a continuation of Ser. No. 217,014, Jul. 8, 1988, Pat. No. 5,000,956, which is a continuation of Ser. No. 23,583, Mar. 9, 1987, abandoned.

[51] Int. Cl.$^5$ .............................................. A61F 13/00
[52] U.S. Cl. .................... 424/449; 424/448; 424/443
[58] Field of Search .................. 424/449, 448, 443

[56] References Cited

U.S. PATENT DOCUMENTS

| | | | |
|---|---|---|---|
| 3,598,122 | 8/1971 | Zaffaroni | 128/268 |
| 3,598,123 | 8/1971 | Zaffaroni | 128/268 |
| 4,130,643 | 12/1978 | Smith | 424/238 |
| 4,144,317 | 3/1979 | Higuchi et al. | 424/21 |
| 4,286,592 | 9/1981 | Chandrasekaran | 128/260 |
| 4,292,303 | 9/1981 | Keith et al. | 424/28 |
| 4,314,557 | 2/1982 | Chandrasekaran | 128/260 |
| 4,343,798 | 8/1982 | Fawzi | 424/240 |
| 4,353,896 | 10/1982 | Levy | 424/195 |
| 4,362,737 | 12/1982 | Schafer et al. | 424/273 |
| 4,379,454 | 4/1983 | Campbell et al. | 604/897 |

FOREIGN PATENT DOCUMENTS

| | | | |
|---|---|---|---|
| 00040861A1 | 12/1981 | European Pat. Off. | A61K 9/70 |
| 0159168A2 | 10/1985 | European Pat. Off. | A61K 47/00 |
| 0196769A2 | 10/1986 | European Pat. Off. | A61L 15/03 |
| 0314528A1 | 5/1989 | European Pat. Off. | |
| 60-23312 | 2/1985 | Japan | A61K 9/70 |
| WO8809175 | 12/1988 | PCT Int'l Appl. | A61K 31/58 |

OTHER PUBLICATIONS

Drug Information 86, 84:06 "Anti-Inflammatory Agents: Topical Corticosteroids General Statement" pp. 1780–1782, American Hospital Formulary Service.

J. Foussereau, C. Benezra, H. I. Maibach & N. Hjorth, "Occupational Contact Dermatitis, Clinical and Chemical Aspects," (W. B. Saunders Company 1982).

B. W. Barry and D. I. D. El Eini, "Influence of non-ionic surfactants on permeability of hydrocortisone, dexamethasone, testosterone and progesterone across cellulose acetate membrane," J. Pharm. Pharmac. 28, pp. 219–227 (1976).

D. V. Belsito et al., "Effect of Glucocorticosteroids on Epidermal Langernans Cells," J. Exp. Med., vol. 155, pp. 291–302.

W. M. Burrows et al., "Inhibition of Induction of Human Contact Sensitization by Topical Clucocorticosteroid," Arch Dermatol, vol. 112, pp. 175–178 (Feb. 1986).

B. Berman et al., "Modulation of Expression of Epidermal Langerhans Cell Properties Following in Situ Exposure to Glucocorticosteroids," The Journal of Investigative Dermatology, vol. 80, No. 3, pp. 168–171 (1983).

"Contact Dermatitis due to Nitroglycerin Ointment," A. A. Hendricks and G. W. Dec Arch. Dermatol. 115:853–855 (1979).

J. Fachet et al., "Effect of Corticosteroids and Adult Thymectomy on Induction and Recall of Contact Sensitivity in Mice," Clin. Exp. Immunol. 10, pp. 661–692 (1972).

Geoffrey Zubay, Biochemistry, pp. 535–543 (1983).

B. Samuelsson, "Leubotrienes: Mediators of Immediate Hypersensitivity Reactions and Inflammation," Science, vol. 220, pp. 568–575.

AMA Drug Evaluations, 5th Edition, pp. 1441–1442.

*Primary Examiner*—Paul R. Michl
*Assistant Examiner*—D. Gabrielle Phelan
*Attorney, Agent, or Firm*—Jean Marie Duvall; Steven F. Stone; Edward L. Mandell

[57] ABSTRACT

A method of preventing sensitization in transdermal drug delivery by the inclusion of a corticosteroid, which will be coextensively coadministered with the sensitizing agent.

8 Claims, 1 Drawing Sheet

PREVENTION OF CONTACT ALLERGY BY COADMINISTRATION OF A CORTICOSTEROID WITH A SENSITIZING DRUG

CROSS-REFERENCE TO RELATED APPLICATIONS

This application is a continuation of U.S. Ser. No. 07/753,284 filed on Aug. 30, 1991, now U.S. Pat. No. 5,171,576 which application is a division of U.S. Ser. No. 07/604,840 filed on Nov. 27, 1990, which issued on Dec. 31, 1991 as U.S. Pat. No. 5,077,054, which application is a continuation of U.S. Ser. No. 07/217,014 filed on Jul. 8, 1988, which issued on Mar. 19, 1991 as U.S. Pat. No. 5,000,956, which application is a continuation of U.S. Ser. No. 07/023,583 filed on Mar. 9, 1987, now abandoned, which applications are incorporated herein by reference, and benefit is claimed of their filing dates. These applications are assigned to the ALZA Corporation of Palo Alto, Calif.

BACKGROUND OF THE INVENTION

1. Field of the Invention

This invention relates to the transdermal delivery of drugs. More particularly, this invention relates to the prevention of contact sensitization. Still more particularly, but without limitation thereto, this invention relates to the coextensive coadministration of corticosteroids and sensitizing drugs.

2. Description of the Prior Art

The transdermal route of parenteral delivery of drugs provides many advantages and transdermal systems for delivering a wide variety of drugs or other beneficial agents are described in U.S. Pat. Nos. 3,598,122, 3,598,123, 4,286,592, 4,314,557, 4,379,454, 4,559,222, and 4,573,995, for example, all of which are incorporated herein by reference.

These transdermal drug delivery systems are well known. In many cases, drugs which would appear to be ideal candidates for transdermal delivery have a tendency to sensitize the patient, leading to skin reactions, a condition known as contact sensitivity or contact allergy. Therefore, despite the development of the art, there has remained a continuing need for improved methods of overcoming sensitization problems.

Sensitization is a two-phase process invloving totally distinct biological mechanisms. The first is the induction phase where the skin is initially exposed to the sensitizing drug. During this phase, generally no skin reaction may be noted. In the induction phase, the sensitizing drug or antigen is presented to the T-lymphocytes by the Langerhans cells of the epidermis, either in situ of in the draining lymph node. As a consequence, cells which recognize the antigen, proliferate and to sme extent differentiate.

The second subsequent phase, following the establishment of contact allergy, is elicitation where subsequent exposure to the sensitizing drug results in a manifested skin reaction. This condition is known as contact dermatitis. During elicitation, the antigen is once again presented mainly on Langerhans cells. The T-cells which have proliferated upon prior exposure now come to the treated site and initiate toxic events which result in local inflammation.

Contact sensitization is a completely different process than irritation. Irritation is caused by and therefore relieved by a different mechanism than that of sensitization. Irritation depends upon a variety of factors including, but not limited to, change in pH and bacterial overgrowth. Ultimately, irritation is the result of damage to the cells by cellular response to a toxic agent, i.e. one that irritates. Sensitization on the other hand, is the result of an allergic cellular response to an agent which is not necessarily intrinsically toxic.

Corticosteroids are commonly used to alleviate the after-effects of elicitation of contact sensitivity and of irritation and are administered either alone or in combination with a drug, for their known anti-inflammatory action, and have successfully worked to diminish the symptoms of: (1) allergic reaction, i.e. after sensitization has occurred, J. Foussereau, C. Benezra, H. I. Maibach & N. Hjorth, Occupational Contact Dermatitis, Clinical and Chemical Aspects (W. B. Saunders Company, 1982); and (2) irritation, Japanese Kokai No. 60-23,312, Nitto Electric Ind. Co. (1985).

However, in general it is difficult to significantly reduce the response once the skin has been sensitized. For that reason, this invention is directed towards "before-the-fact" effectiveness, i.e. reduction or elimination of the induction phase of sensitization before serious reactions occur, rather than treating problems after pain and discomfort have occurred.

Corticosteroids are well known to reduce inflammation caused by irritation. For example, in Japanese Kokai No. 60-23,312, corticosteroids are used to prevent inflammation due to retained moisture. As to alleviation of the elicited allergic reaction as noted above, corticosteroids work to slightly reduce inflammation but do not exhibit their full anti-inflammatory effects until most of the sensitizing drug has been removed from the sensitized area.

Accordingly, prior to our invention, the topical application of corticosteroids either alone or in combination with other drugs, was not known to provide any beneficial effect during the induction phase of sensitization and was even contraindicated because it tended to mask the elicitation phase. See Drug Information 86, 84:06, "Anti-Inflammatory Agents: Topical Corticosteroids General Statement", at page 1781, pp 1780–82, American Hospital Formulary Service (1986).

For the above stated reasons, our discovery that corticosteroids coadministered with sensitizing drugs according to our invention, actually prevents the induction of sensitization, is truly unobvious.

According to our invention, we have found that coextensive coadministration of a corticosteroid with a drug which tends to sensitize the skin upon prolonged exposure, can prevent the induction phase of sensitization or reduce it significantly. This is distinguishable from agents which act to reduce irritation.

SUMMARY OF THE INVENTION

An object of the present invention is to prevent contact sensitization inherent in the transdermal administration of numerous drugs.

A further object of the present invention is to eliminate the induction phase of sensitization.

These and other objects have been demonstrated by the present invention wherein a sensitizing drug and a corticosteroid are transdermally coadministered as a composition of matter which may take the form of a matrix in a transdermal therapeutic system or of a formulation applied to the skin as an ointment, gel or cream.

DESCRIPTION OF THE PREFERRED EMBODIMENT

Figure 1:
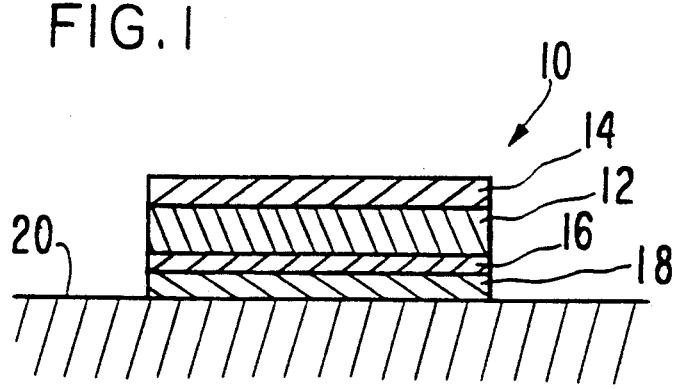
FIG. 1 is a cross-sectional view of one embodiment of a transdermal therapeutic system according to this invention.

According to our invention, we have discovered that continually coadministering a corticosteroid with drugs and other beneficial agents, will prevent the occurrence of the induction phase of sensitization. In order to produce the effects obtained herein which are not obtained according to the prior art: (1) the corticosteroid must be delivered at therapeutically effective rates, i.e. sensitization induction preventing rates, or in therapeutically effective amounts and; (2) the corticosteroid must be delivered at such rates throughout the period during which the drug is present in the skin. These two features distinguish our invention from the prior art in which insufficient corticosteroid was present, the corticosteroid was not present in a form transdermally administrable at the required rates or both.

In one embodiment of our invention, both the drug and the corticosteroid are simultaneously delivered for the entire delivery period, i.e. coextensive coadministration. In another embodiment of this invention, coextensive coadministration is preceded by delivery of the corticosteroid alone, for a specified period of time. In still another embodiment of the invention, the corticosteroid is delivered for a portion of the time in which the drug is delivered.

As used herein the term "drug" relates to a biologically active agent, compound or composition of matter which is administered for the purpose of providing some beneficial or therapeutic effect. As used herein, the term "transdermal" delivery relates to the delivery of a drug by passage through skin or mucosa by topical application.

According to our invention, a corticosteroid and the sensitizing drug to be delivered are placed in drug and corticosteroid transmitting relationship to the appropriate body surface, preferably in a carrier therefore, and maintained in place for the desired period of time. The drug and corticosteroid are typically dispersed within a physiologically compatible matrix or carrier which may be applied directly to the body as an ointment, gel, cream, suppository or sublingual or buccal tablet, for example, but are more preferably administered from a transdermal therapeutic system as more fully described below.

This invention has proven utility in connection with the delivery of chlorpheniramine maleate. It is anticipated that coadministration of a corticosteroid according to our invention with known sensitizing drugs such as clonidine, tetracaine, naloxone, naltrexone and nalbuphine along with narcotic analgesics such as buprenorphine, hydromorphone and levorphanol, will prevent sensitization. It is also anticipated that this invention has utility in connection with the delivery of drugs within the broad class normally delivered through body surfaces and membranes, including skin. In general, this includes therapeutic agents in all of the major therapeutic areas including, but not limited to, anti-infectives, such as antibiotics and antiviral agents, analgesics and analgesic combinations, anorexics, antiarthritics, antiasthmatic agents, anticonvulsants, antidepressants, antidiabetic agents, antidiarrheals, antihistamines, anti-inflammatory agents, antimigraine preparations, antimotion sickness preparations, antinauseants, antineoplastics, antiparkinsonism drugs, antipruritics, antipsychotics, antipyretics, antispasmodics, including gastrointestinal and urinary; anticholinergics, sympathomimetics, xanthine derivatives, cardiovascular preparations including calcium channel blockers, beta-blockers, antiarrythmics, antihypertensives, diuretics, vasodilators, including general, coronary, peripheral and cerebral, central nervous system stimulants, cough and cold preparations, decongestants, diagnostics, hormones, hypnotics, immunosuppressives, muscle relaxants, parasympatholytics, parasympathomimetics, psychostimulants, sedatives and tranquilizers.

The invention is best understood when viewed in light of the following relationships. For a given drug delivery system, certain parameters are predetermined. One such parameter is the therapeutically effective drug delivery rate, $J_d$ ($\mu g/cm^2$-hr). Given a set delivery time period t (hrs). the amount of drug which will be delivered per unit area $x_d$ ($\mu g/cm^2$) can be determined. In such systems, a sufficient amount of drug exists in the reservoir to maintain the necessary concentration gradient which acts as the driving force to maintain said rate for the predetermined time, t (hrs). Normally, an excess of drug over saturation is used when a constant steady drug delivery rate is desired. Typically, this excess is calculated by determining the amount of drug needed to have a saturated system and adding to this value, the amount of drug which is going to be delivered ($x_d$) and an excess to act as a "safety factor" to provide continuous delivery at the required rates. The delivered amount is shown by the equation $x_d/J_d = t$ or $x_d = (J_d)(t)$.

In this invention, the corticosteroid preferably is continuously coadministered, i.e. as long as the sensitizing drug is either being delivered or is present in the skin, the corticosteroid is also being delivered. An important parameter is the induction preventing rate $J_c$ ($\mu g/cm^2$-hr) which is essentially the corticosteroid delivery rate. The $J_c$ value is the net delivery rate, taking into account the use of any permeation enhancers which help to achieve that rate. Since the time t has already been determined by the therapeutic requirements of the system, the basic equation is $x_d/J_d = t = x_c/J_c$, where $x_c$ is the amount of corticosteroid per unit area which will be delivered to the skin. Just as with the drug, the corticosteroid must be present in excess, to provide that the corticosteroid is continuously delivered with the drug and continues to be present as long as any drug is present in the epidermis. Therefore, for a system where $J_d$, $x_d$, t and $J_c$ are known, the amount of corticosteroid to be placed in the system can be determined by calculating the amount needed to saturate the system plus the amount which is to be delivered ($x_c = (J_c)(t)$), plus an excess amount as a "safety factor".

Especially good results have been achieved using hydrocortisone as the corticosteroid. Hydrocortisone esters such as hydrocortisone acetate, are also suitable. More potent corticosteroids may not require a permeation enhancer as hydrocortisone and hydrocortisone acetate do. However, the advantages of hydrocortisone or its esters such as hydrocortisone acetate, is that they do not damage the skin upon prolonged exposure and they are approved for over-the-counter use. This invention contemplates the use of any corticosteroid in addition to hydrocortisone and includes, without limitation, beclomethasone, betamethasone, benzoid, betamethasone dipropionate, betamethasone valerate, clobetasol propionate, clobetasol butyrate, desonide, dexamethasone, fluocinonide, prednisolone and triamcinolone, for example.

The necessary concentration of corticosteroid in the epidermis can be achieved by the addition of flux enhancers and controlled release of the steroid. The desired flux rate of the corticosteroid will vary from corticosteroid to corticosteroid, but is typically about 0.01 to 5 pg/cm$^2$-hr. For certain corticosteroids, this flux rate can be obtained without the addition of permeation enhancers. However, with corticosteroids such as hydrocortisone and hydrocortisone esters, a permeation enhancer is usually necessary to achieve the desired flux rate. Suitable permeation enhancers for corticosteroids are known to the art and include, without limitation, oily surfactants such as sucrose monolaurate and glycerol monooleate, alcohols and keratinolgtic agents.

One embodiment of this invention is the transdermal delivery of a sensitizing drug and a corticosteroid by application of a formulation to the skin surface, which may be aqueous or non-aqueous based. These formulations can be designed to deliver the sensitizing drug and the corticosteroid at the desired fluxes and can be in numerous forms% including without limitation, ointments, gels and creams.

Aqueous formulations, specifically gels, typically comprise water and about 1-2 weight % of a gelling agent such as hydroxyethyl cellulose or hydroxypropyl cellulose. Typical non-aqueous gels are comprised of silicone fluid or mineral oil, the latter of which may also have 1-2 weight % of a gelling agent such as colloidal silicon dioxide. The suitability of a particular gel depends upon the compatibility of its constituents with both the sensitizing drug and corticosteroid, along with the permeation enhancer, if any.

EXAMPLE I

Testing protection from sensitization by use of hydrocortisone, was done on two groups (40 subjects each) of adult females. Group I received gels containing, by weight percent: 8% dex-chlorpheniramine maleate (DCPM), 2% hydrocortisone, 5% sucrose monolaurate, 4% hydroxyethyl cellulose and 81% water. Group II received gels containing, by weight percent: 8% DCPM, 4% hydroxyethyl cellulose and 88% water.

These gel applications contained up to 25 mg DCPM and provided a DCPM transdermal permeation rate of about 10-15 μg/cm$^2$-hr. The drug concentration was such that, as calculated from results of skin permeation studies using human skin in vitro, the transdermal permeation rate of DCPM was no greater than 0.72 mg/day. For the gels containing hydrocortisone, the flux rate of corticosteroid was about 0.5-1.0 μg/cm$^2$-hr or up to 0.05 mg/day for a 2 cm$^2$ system.

Gels were placed in standard 2 cm$^2$ patch test devices, and applied for three weeks to the same spot, exchanging about every other day. Two weeks after removal of the ninth gel, subjects received an application of the gel to which they had been previously exposed, to a new skin area. Forty-eight hours later, the gel was removed and another, similar one, applied to the same area. After an additional 48 hours of residence, the second gel was removed.

Reactions were observed 48 and 96 hours after the last removal. The results were as follows: in Group II, 16 subjects experienced sensitization, while in Group I which used the gel containing hydrocortisone, only 2 subjects experienced any sensitization. In this manner, coadministration of hydrocortisone prevents topical sensitization to DCPM prophylactically.

EXAMPLE II

A challenge was done to the experiment described in Example I. As stated above, of the 40 subjects in Group I (drug plus hydrocortisone) 2 experienced sensitization, leaving 38 who were not sensitized. Of the 40 subjects in Group II (drug alone) 16 subjects experienced sensitization, leaving 24 who were not sensitized.

Approximately one month after the completion of the experiment in Example I, the subjects who had not become sensitized were once again subjected to the same test conditions as before, except that both groups received both test items, i.e. DCPM gels alone and DCPM gels containing hydrocortisone. Of the 38 subjects in Group I, 1 subject responded and of the 24 subjects in Group II, 2 responded. All three of these subjects responded to both test items, indicating that once sensitized, the presence of hydrocortisone does not prevent a skin reaction in the allergic individual.

Combining the long term evaluation results of the original and the challenging experiment reveals that of 40 subjects receiving a gel containing dex-chlorpheniramine and hydrocortisone, only 3 experienced any sensitization. Of the 40 receiving a gel containing dex-chlorpheniramine alone, 18 became sensitized. The challenge to the results of Example I was done to prove that hydrocortisone specifically, and corticosteroids generally, suppress the induction phase of sensitization, not the elicitation phase.

Referring now to FIG. 1, a transdermal therapeutic system 10 according to this invention is shown. The system 10 comprises a sensitizing drug reservoir 12 covered by an impermeable backing 14, and a rate controlling membrane 16. The system 10 adheres to the surface of the skin 20 by means of an in-line contact adhesive 18. This adhesive layer 18 contains a set amount of corticosteroid. A strippable release liner, not shown, adapted to be removed prior to application would normally be included in the packaged product.

Figure 2:
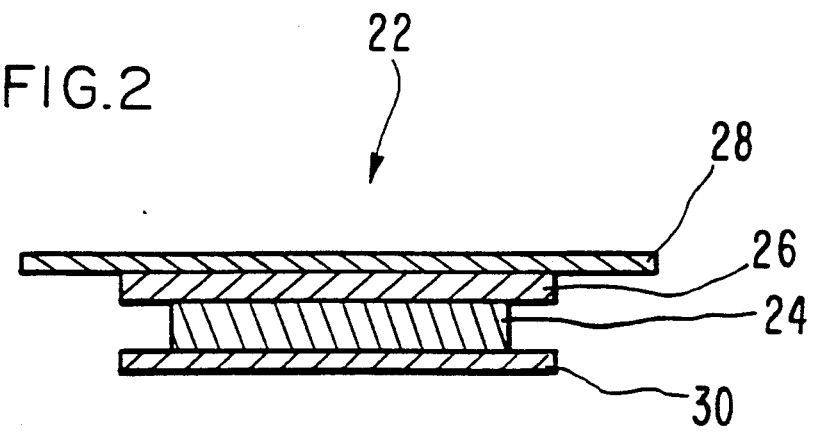
FIG. 2 is a cross-sectional view of another embodiment of a transdermal therapeutic system according to this invention.

In an alternate embodiment, the system is attached by means of an adhesive overlay, as is shown in FIG. 2. The system 22 is comprised of a sensitizing drug/ corticosteroid reservoir 24 which is in the form of a matrix or carrier having the drug and the corticosteroid dispersed throughout. The reservoir 24 is covered by an impermeable backing 26 which is preferably sized larger in circumference than the reservoir 24. Means 28 for maintaining the system on the skin may be fabricated together with or provided separately from the remaining elements of the system. Means 28 as illustrated in FIG. 2 takes the form of an adhesive overlay. In some instances, an adhesive overlay 28 is preferable over an in-line contact adhesive 18 as shown in FIG. 1. This is true when there are elements present in the matrix which may adversely affect the adhesive properties of most pharmaceutically acceptable contact adhesives. For this reason, impermeable backing layer 26 is preferably sized slightly larger than the reservoir 24 to provide a peripheral area around the reservoir 24, which would be free of any material which may seep from under the base of reservoir 24 and adversely interact with the adhesive in overlay 28. A strippable release liner 30 would also be provided with the system 22, to be removed prior to use.

Various materials suited for the fabrication of the various layers are disclosed in the aforementioned patents. The composition of the matrix may, depending on the drug to be delivered, be either an aqueous or anhydrous base. Suitable matrices or carriers are described in the above identified patents and include, without limitation, natural and synthetic rubbers such as polybutylene, polyisobutylene, polybutadiene, polyethylene, styrenebutadiene copolymers, polyisoprene, polyurethane, ethylene/propylene copolymers, polyalkylacrylate polymers, copolyesters, ethylene/acrylic copolymers, silicones and butadiene/acrylonitrile copolymers for example and other polymers such as the ethylene vinylacetate (EVA) polymers described in U.S. Pat. No. 4,144,317 (which is incorporated herein by reference). Other suitable materials include gelled or thickened mineral oil, petroleum jelly and various aqueous gels and hydrophilic polymers. Typically the drug is dispersed through the matrix or carrier at a concentration in excess of saturation, the amount of excess being a function of the intended useful life of the system. The drug may, however, be present at initial levels below saturation without departing from this invention.

In addition to the sensitizing drug and the corticosteroid, which are essential to the invention, the matrix may also contain other materials such as dyes, pigments, inert fillers, permeation enhancers, excipients and other conventional components of pharmaceutical products or transdermal therapeutic systems known to the art.

This invention does not require any pretreatment of the skin site with the corticosteroid. Inclusion of the corticosteroid can be in the drug reservoir and/or other drug releasing compartment of a transdermal therapeutic system. In some instances, there is great disparity between the drug flux and the corticosteroid flux. In such cases, the corticosteroid is preferably placed in the adhesive, as in FIG. 2. On the other hand, where there is no great disparity in fluxes, both the drug and the corticosteroid may be placed together in the reservoir, as in FIG. 1.

The applications and usefulness of this invention as it applies to transdermal systems is best understood in light of the following examples.

EXAMPLE III

Clonidine transdermal drug delivery systems have been found to elicit contact dermatitis in a significant number of patients, to whom the systems are repeatedly applied.

A transdermal therapeutic system as described with respect to FIG. 1 for the delivery of clonidine would be suitable for use in eliminating sensitization caused by clonidine. The system 10 would be fabricated using hydrocortisone as the corticosteroid. Hydrocortisone would be present both in the reservoir 12 and in the adhesive 18. The hydrocortisone would be present in the adhesive layer 18 in an amount in excess of saturation as the adhesive acts as the hydrocortisone reservoir. However, hydrocortisone may also be present to some degree in the drug reservoir 12. Coadministration of hydrocortisone with clonidine is expected to counter any topical sensitization to the drug.

Typical clonidine delivery systems are described in Enscore, et al, U.S. Pat. No. 4,559,222 incorporated herein by reference. A typical release rate in vitro at 32° C. for clonidine is 1.6 $\mu g/cm^2$-hr. For a 7 day (168 hour) delivery system, assuming hydrocortisone is being delivered at a rate in the range of 0.5-1.0 $\mu g/cm^2$-hr, at least 84-168 $\mu g/cm^2$ of hydrocortisone will be delivered during the 7 days. To maintain the necessary concentration gradient driving force, hydrocortisone must be present in the adhesive in a concentration in excess of saturation. The excess must be at least 84-168 $\mu g/cm^2$, the amount of hydrocortisone to be delivered in a 7 day period, in order to attain continuous administration of hydrocortisone and thereby prevent the induction of sensitization.

EXAMPLE IV

U.S. Pat. No. 4,559,222 also describes a scopolamine drug delivery system. Just as with the clonidine system of Example III, a 7 day system for example, would require a saturation concentration plus at least 84-168 $\mu g/cm^2$ of hydrocortisone in the adhesive layer of the system.

EXAMPLE V

Tetracaine is also known to elicit sensitization. A transdermal therapeutic system as described with respect to FIG. 2 for the delivery of tetracaine would be suitable for use in eliminating the sensitization caused by tetracaine. The system 22 would comprise a reservoir 24 containing the tetracaine and an appropriate corticosteroid, such as hydrocortisone. Coadministration of the corticosteroid with tetracaine is expected to counter any sensitization to the drug.

As stated above in Examples III and IV, for a 7 day delivery system, given a hydrocortisone delivery rate in the range of 0.5-1.0 $\mu g/cm^2$-hr, at least 84-168 $\mu g/cm^2$ of hydrocortisone will be delivered during the 7 days. To maintain the necessary driving force, saturation concentration plus at least 84-168 $\mu g/cm^2$ of hydrocortisone would be required to prevent the induction phase of sensitization.

EXAMPLE VI

Transdermal drug systems for the delivery of naloxone, naltrexone and nalbuphine have also been found to elicit sensitization in some patients to whom the systems are repeatedly applied. Typical systems are disclosed in Cheng, et al, U.S. Pat. No. 4,573,995, incorporated herein by reference.

A transdermal therapeutic system as described with respect to FIG. 2 for the delivery of these drugs in their base form would be suitable for use in eliminating the sensitization caused by the drug. The system 22 would comprise a reservoir 24 containing the base form of naloxone, naltrexone or nalbuphine and an appropriate corticosteroid, such as beclomethasone. Coadministration of the corticosteroid with the drug is expected to counter any sensitization to the drug.

As stated earlier, suitable corticosteroid flux rates are about 0.01-5.0 $\mu g/cm^2$-hr. For a 7 day delivery system using beclomethasone, at least 1.68-840 $\mu g/cm^2$ of beclomethasone will delivered during the 7 days. To maintain the driving force then, beclomethasone must be present in the system in excess of its saturation concentration, said excess being at least 1.68-840 $\mu g/cm^2$.

Additionally, since the chemical make-up of some narcotic analgesics such as levorphanol, hydromorphone and buprenorphine is similar to that of naloxone, naltrexone and nalbuphine, it is expected that the sensitization which they induce, will likewise be prevented by the inclusion of a corticosteroid as described by this invention.

The transdermal coadministration of clonidine, scopolamine, tetracaine, naloxone, naltrexone, nalbuphine, levorphanol, hydromorphone and buprenorphine with a corticosteroid, according to our invention, can also be achieved by means of a gel as in Example I. The sensitizing drug, corticosteroid and permeation enhancer (if necessary) can be incorporated in a typical aqueous or non-aqueous gel. The amount of drug incorporated into the gel composition is determined by the therapeutic delivery rate needed for effective treatment. The amount of corticosteroid, on the other hand, is determined by the duration of drug delivery in that the corticosteroid is present in the gel in an amount sufficient for continuous coadministration with the drug.

This invention has been described in detail with further reference to certain preferred embodiments thereof, but it will be understood that variations and modifications can be effected within the spirit and scope of the invention.

What is claimed is:

1. A method of preventing human skin from becoming sensitized by a skin sensitizing drug which is transdermally administered to a human in need thereof, comprising:
    placing a matrix, which matrix contains a composition of matter comprising the sensitizing drug and a corticosteroid, in drug-transmitting and corticosteroid-transmitting relationship to a selected skin site;
    administering said drug at a therapeutically effective rate to the selected skin site over a predetermined period of time; and
    coadministering said corticosteroid to the selected skin site at a sensitization induction preventing rate and over at least the same predetermined period of time.

2. The method of claim 1 wherein said coadministration of drug and corticosteroid to the selected skin site is preceded by delivery of said corticosteroid to the selected skin site without coadministering said drug, for a specified period of time.

3. The method of claim 1 wherein said corticosteroid is administered at a sensitization induction preventing rate within the range of about 0.01–5 $\mu g/cm^2$-hr.

4. The method of claim 3 wherein said corticosteroid is administered to the skin site at said rate throughout the period during which said drug is administered to the skin site.

5. The method of claim 1 wherein said corticosteroid is selected from the group consisting of hydrocortisone, hydrocortisone acetate and hydrocortisone easters.

6. The method of claim 1 wherein said corticosteroid is administered to the selected skin site at a sensitization induction preventing rate by codelivering the corticosteroid with a skin permeation enhancer to the selected skin site.

7. The method of claim 6 wherein said sensitization induction preventing rate is within the range of about 0.5–1.0 $\mu g/cm^2$-hr.

8. The method of claim 1, wherein the sensitizing drug is selected from the group consisting of clonidine, scopolamine, tetracaine, chlorpheniramine maleate, naloxone, naltrexone, nalbuphine, levorphanol, hydromorphone, and buprenorphine; and the corticosteroid is selected from the group consisting of hydrocortisone, hydrocortisone acetate and hydrocortisone esters.

* * * * *